United States Patent [19]

Pols et al.

[11] Patent Number: 4,463,761
[45] Date of Patent: Aug. 7, 1984

[54] ORTHOPEDIC SHOE

[76] Inventors: Sidney Pols, c/o E. J. Sabel Co., Benson East Building, P.O. Box 644, Jenkintown, Pa. 19046; Eugene L. Schultz, 100 DeVille Cir., Williamsville, N.Y. 14221

[21] Appl. No.: 404,607

[22] Filed: Aug. 2, 1982

[51] Int. Cl.³ .............................................. A61F 5/14
[52] U.S. Cl. ......................................... 128/581; 36/88
[58] Field of Search ............... 128/89 R, 90, 581, 595, 128/80 R; 36/87, 88; 2/DIG. 6

[56] References Cited

U.S. PATENT DOCUMENTS

| | | | |
|---|---|---|---|
| 2,961,714 | 11/1960 | Murray | 128/90 X |
| 3,613,271 | 10/1971 | Geller | 36/87 X |
| 3,823,493 | 7/1974 | Brehm et al. | 36/87 X |
| 4,053,995 | 10/1977 | Shein | 36/88 |

Primary Examiner—John D. Yasko
Attorney, Agent, or Firm—Z. T. Wobensmith, III

[57] ABSTRACT

An orthopedic shoe for use by a person who has a moderate deformity of the foot, which shoe can be of stock size and width, and is moldable to the foot of the wearer by previous heat application to accommodate the deformity.

9 Claims, 11 Drawing Figures

ORTHOPEDIC SHOE

BACKGROUND OF THE INVENTION

1. Field of the Invention

This invention relates to an orthopedic shoe of the moldable type.

2. Description of the Prior Art

For those persons who have moderate deformities of the foot which could be congenital, arthritic, diabetic or related to other conditions, it has been difficult to obtain instock shoes that are comfortable and at a moderate cost. The person who suffers from foot deformities typically would go to a custom shoe shop where measurements and a cast would be made of the foot. The cast is sent to a factory where the shoes would be handmade to conform to the configuration or shape of the cast and the shoes sent to the custom shop to which the customer would have to return and have the shoes fitted to his or her foot. This procedure is both time consuming and very costly. The shoe of our invention can be carried in stock sizes and widths on the shelf, in a shoe store, selected, fitted and molded to the customer in one visit and at a cost far below that of custom molded shoes available from others.

SUMMARY OF THE INVENTION

This invention relates to an orthopedic shoe for use by a person with a moderate foot deformity, which shoe is shaped or molded to the foot of the wearer at the time of purchase.

The principal object of the invention is to provide an orthopedic shoe that can be quickly and easily fitted to the foot or feet of a wearer.

A further object of the invention is to provide a shoe of the character aforesaid which can be carried in stock by a shoe store with a full range of sizes and widths.

A further object of the invention is to provide a shoe of the character aforesaid which can be molded by hand to the foot of the wearer or which can be shaped or molded by use of heating and shaping tools.

A further object of the invention is to provide a shoe of the character aforesaid that is comfortable, durable and long wearing.

A further object of the invention is to provide a shoe of the character aforesaid which may have a removable insole available in varying thicknesses and that will be moldable to the plantar surface of the foot.

Other objects and advantageous features of the invention will be apparent from the description and claims.

DESCRIPTION OF THE DRAWINGS

The nature and characteristic features of the invention will be more readily understood from the following description taken in connection with the accompanying drawings forming part hereof in which.

Figure 1:
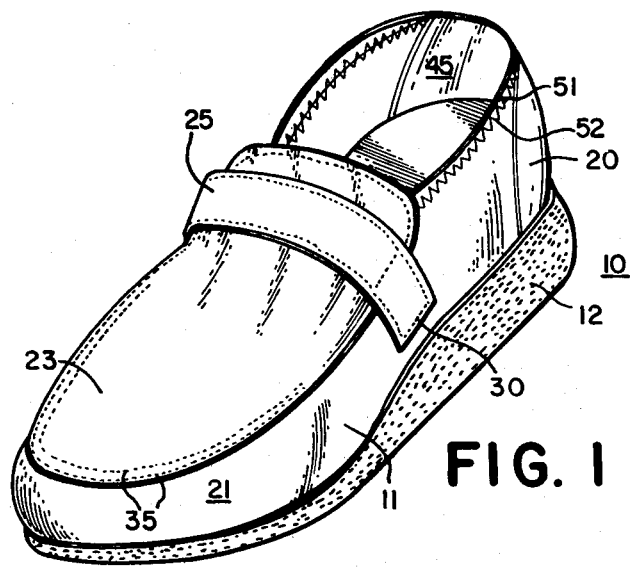
FIG. 1 is a view in perspective of one embodiment of the orthopedic shoe of our invention.
Figure 2:
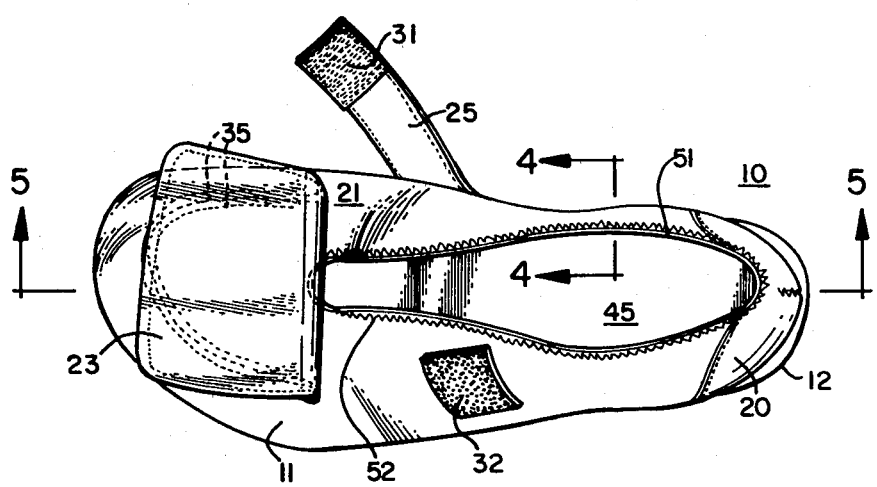
FIG. 2 is a top plan view of the orthopedic shoe shown in FIG. 1.

It should, of course, be understood that the description and drawings herein are illustrative merely, and that various modifications and changes can be made in the structure disclosed without departing from the spirit of the invention.

Like numerals refer to like parts throughout the several views.

DESCRIPTION OF THE PREFERRED EMBODIMENTS

Referring now more particularly to the drawings and FIGS. 1-8, inclusive, one embodiment of orthopedic shoe 10 includes an upper 11, and a sole 12 attached thereto in any desired manner and preferably by cementing the sole 12 to the upper 11. The sole 12 is preferably formed of a resilient relatively stiff spongy material, resistant to moisture, with a flat bottom surface 14 which can have a non-slip pattern 15 thereon of well known type.

An insert 17 is provided inside upper 11 which extends longitudinally and transversely across the sole 12 to the upper 11 and can be of leather or man-made material as desired and secured to the sole 12 by fasteners 18.

The upper 11 is shown of multipiece construction, with a heel portion 20, outer side and front portion 21, tongue 23 and a strap 25.

Figure 6:
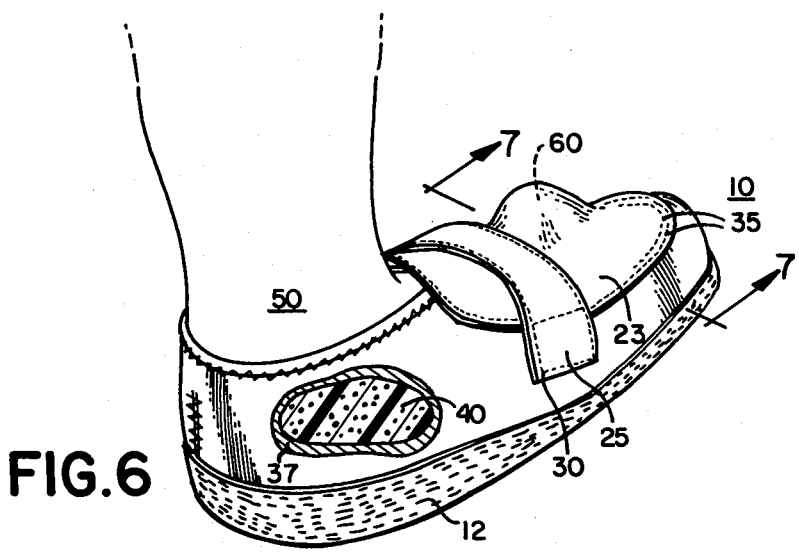
FIG. 6 is a rear elevational view partly broken away of the orthopedic shoe of FIG. 1 in place on the foot of a wearer.

The strap 25 as shown in FIG. 6 is fastened to the right side of the portion 21 by a line of stitching 30 and has a strip of thistle cloth 31 at the opposite end, of well known type, such as "Velcro," shown as engaged with a complimentary strip 32 of thistle cloth on the left side of the portion 21.

The tongue 23 is fastened to the outer side and front portion 21 by a double line of stitches 35, and the heel portion 20 is fastened to the portion 21 by a line of stitches 36.

The upper 11 includes an outer layer 37 of leather or synthetic plastic and an inner lining 40 of synthetic plastic, which can be any suitable well known close linked closed cell polyethylene foam. The lining 40 is bonded to the layer 37 in any desired manner such as chemical bonding. The upper 11 has an opening 45 for insertion of a foot 50, and has a strip 51 which extends therearound and is secured thereto by a line of stitching 52.

Figure 3:
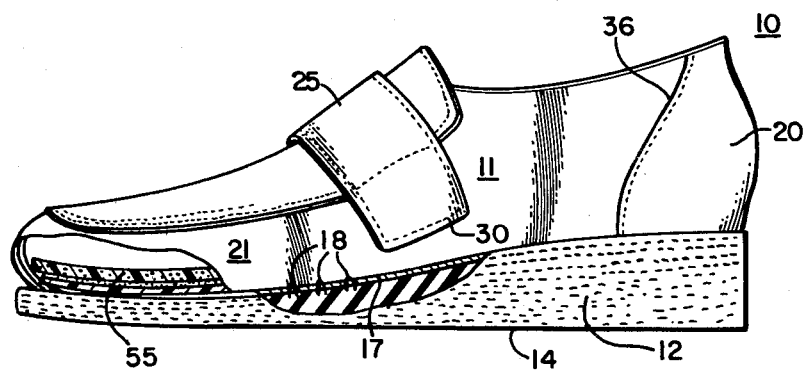
FIG. 3 is a side elevational view of the orthopedic shoe of FIG. 1.
Figure 8:
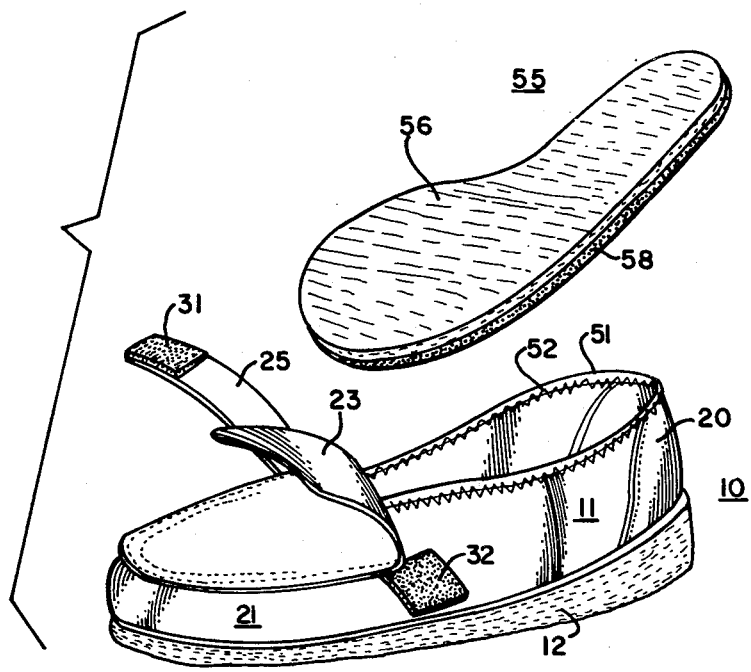
FIG. 8 is an exploded perspective view of the orthopedic shoe of FIG. 1.

As shown in FIGS. 3 and 8, the shoe 10 can be provided with a removable insole 55 which is illustrated of integral multi-piece construction, but which can be of any number of pieces separated or integral to obtain the desired thickness depending on the need of the wearer. The insole 55 as shown has a top piece 56 of leather or man-made material, and a bottom piece 54 of polyethylene foam.

The upper 11 can be constructed of leather, or of urethane if greater resistance to moisture is required.

Figure 9:
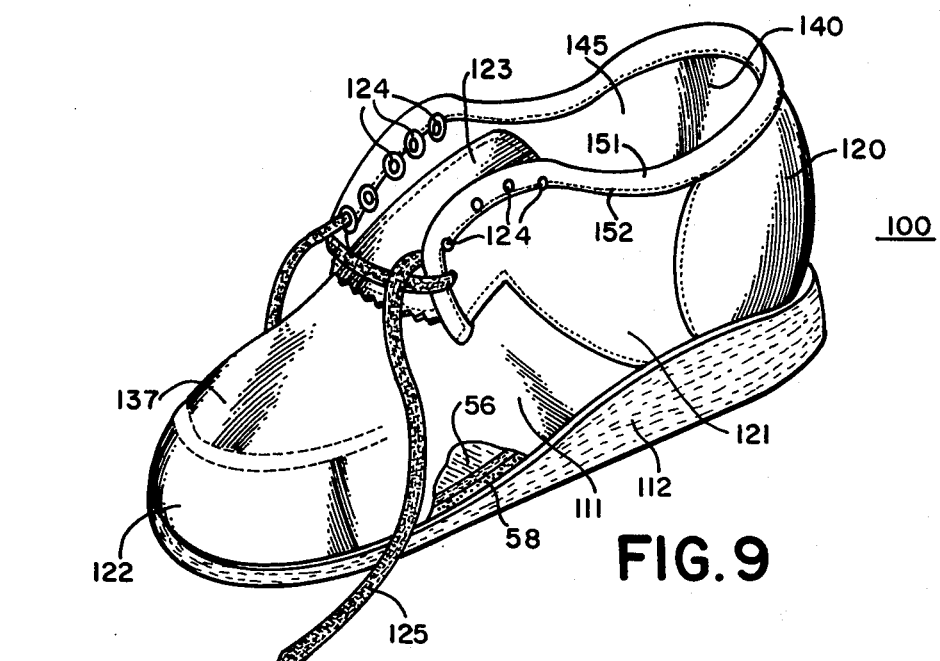
FIG. 9 is a view in perspective of another embodiment of the orthopedic shoe of our invention.
Figure 10:
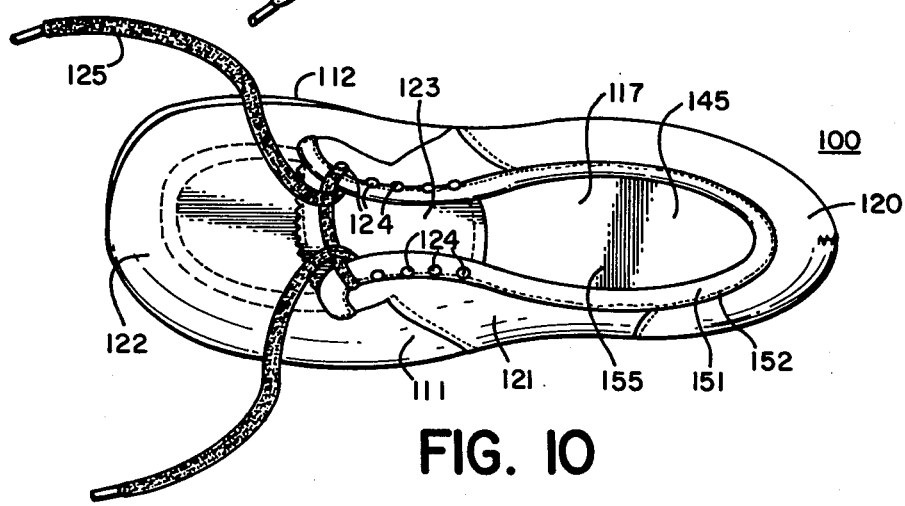
FIG. 10 is a top plan view of the orthopedic shoe of FIG. 9.

Referring to FIGS. 9 and 10, another embodiment of orthopedic shoe 100 is illustrated which includes an upper 111, and a sole 112 attached thereto in any desired manner as described for shoe 10. The shoe 100 can be provided with an insert 117 similar to insert 17 as desired. The upper 111 is of multi-piece construction, with a heel portion 120, side portion 121, front portion 122, and tongue 123. The side portions 121 are shown as provided with eyelets 124 of conventional type through which a shoe lace 125 is threaded in conventional manner. The upper 111 is constructed similar to upper 11 of shoe 10 with an outer layer 137 of leather or synthetic plastic and an inner lining 140 of synthetic plastic which can be of any suitable well known close linked cell polyethlene foam bonded to layer 137 in any desired manner.

The upper 111 has an opening 145 for insertion of a foot (not shown) and has a strip 151 extending around the opening 145 fastened to the upper leg a line of stitches 152. The shoe 100 can be provided with a removable insole 155 as described for insole 55.

Figure 11:
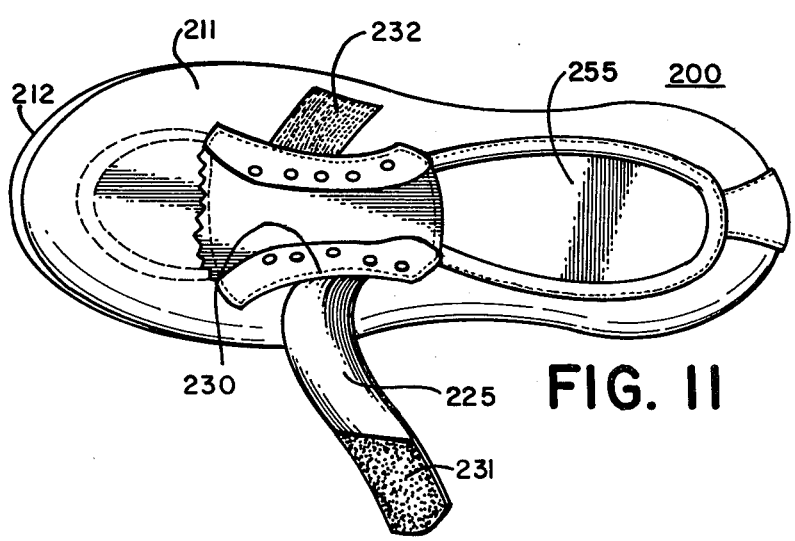
FIG. 11 is a top plan view of still another embodiment of the orthopedic shoe of our invention.

Referring now to FIG. 11, another embodiment of shoe 200 is illustrated with an upper 211, sole 212, and insole 255 as described for shoe 100. Shoe 200 can be constructed like shoe 100, but is additionally provided with a strap 225 fastened to the upper 211 at one end by a line of stitches 230 and with a strip of thistle cloth 231 at the opposite end of well known type, such as "Velcro" shown as engaged with a complimentary strip 232 of thistle cloth secured to the other side of upper 211.

Figure 7:
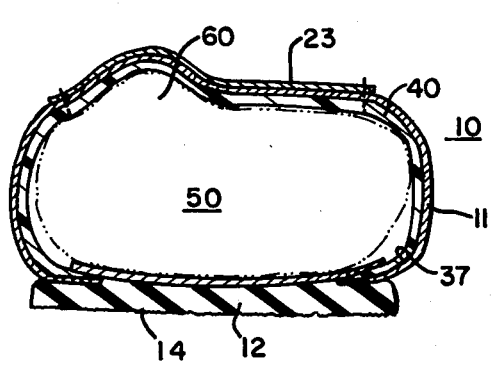
FIG. 7 is a vertical sectional view taken approximately on the line 7—7 of FIG. 6.
Figure 4:
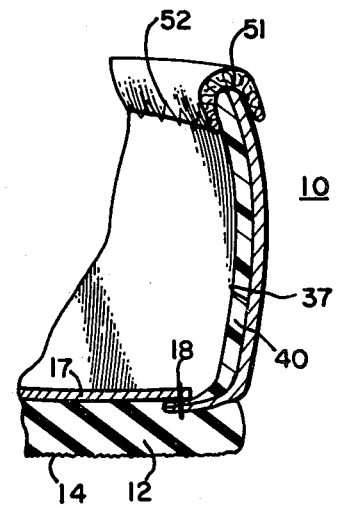
FIG. 4 is a fragmentary, vertical, sectional view taken approximately on the line 4—4 of FIG. 2.
Figure 5:
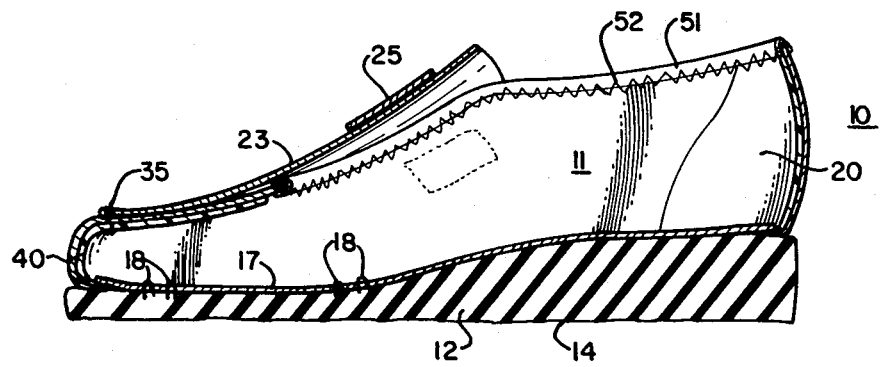
FIG. 5 is a vertical sectional view taken approximately on the line 5—5 of FIG. 2.

Referring now specifically to FIGS. 6 and 7, it will be noted that shoe 10 is in place on the foot 50 of a wearer (not shown), which foot 50 has a protrusion 60 which the shoe 10 has accommodated. The mode of operation will now be pointed out.

The shoes 10, 100 or 200 are made up in the factory as described to the various stock sizes and widths normally carried by shoe stores. When a person desires to purchase a pair of the shoes 10, 100 or 200, he or she proceeds to the shoe store where the correct shoe in length and width is selected.

The desired lift is determined and one or more insoles 55, as desired, are inserted into the shoe 10 for the comfort of the wearer, and to provide the desired degree of lift. The shoe salesman notes the location of the deformity 60 and heats the shoe 10 in an oven (not shown) to approximately 200 degrees for two or three minutes. The shoe is then removed from the oven and placed on the wearer's foot 50, where it is molded to the deformity, such as protrusion 60, by the hands of the salesman. The shoe cools sufficiently by the time it goes from the oven (not shown) to the wearer's foot 50 that it is not too hot to handle, but is still warm enough to be molded. If the deformity is too large to be accommodated by hand, then heating and shaping tools (not shown) of well known type are used to form the shoe to conform to the deformity or deformities.

The shoes 100 or 200 can be shaped and molded to the customer's foot (not shown) as described for shoe 10.

It will thus be seen that an orthopedic shoe has been provided with the objects of the invention are attained.

We claim:

1. An orthopedic shoe capable of being fitted and molded on and to the foot of a wearer which comprises
   an upper of multi-piece construction comprising
   an outer layer having an inner lining bonded thereto,
   said upper being designed to extend over the foot of the wearer, and capable of being softened by heat to be moldable to at least one deformity of the foot of the wearer, and
   a sole having a flat bottom surface and which is joined to the upper.

2. An orthopedic shoe as defined in claim 1 in which said upper is constructed or moldable synthetic plastic.

3. An orthopedic shoe as defined in claim 1 in which said lining is of moldable close linked closed cell polyethylene foam.

4. An orthopedic shoe as defined in claim 1 in which said outer layer is of leather.

5. An orthopedic shoe as defined in claim 1 in which said outer layer is of synthetic plastic.

6. An orthopedic shoe as defined in claim 1 in which a removable multi-layer insole is provided.

7. An orthopedic shoe as defined in claim 6 in which said insole includes at least one layer of close linked closed cell polyethylene foam.

8. An orthopedic shoe as defined in claim 1 in which a closure is provided comprising thistle cloth.

9. An orthopedic shoe as defined in claim 1 in which eyelets are provided in said upper and
   a shoe lace is provided threaded through said eyelets providing a closure.

* * * * *

UNITED STATES PATENT AND TRADEMARK OFFICE
CERTIFICATE OF CORRECTION

PATENT NO. : 4,463,761

DATED : August 7, 1984

INVENTOR(S) : Pols et al.

It is certified that error appears in the above-identified patent and that said Letters Patent is hereby corrected as shown below:

Column 2,

Line 67, after "piece", "54" should be - 58 -

Column 4,

Line 29, after "constructed", "or" should be

- of -

Signed and Sealed this

Twenty-sixth Day of February 1985

[SEAL]

Attest:

DONALD J. QUIGG

*Attesting Officer*   *Acting Commissioner of Patents and Trademarks*